United States Patent
Hock et al.

(10) Patent No.: US 7,176,285 B2
(45) Date of Patent: Feb. 13, 2007

(54) HISTIDINE PHOSPHATASE INTERACTING PROTEIN WITH 120KD

(75) Inventors: Bjoern Hock, Maintal (DE); Klaus Duecker, Darmstadt (DE); Roland Kellner, Heppenheim (DE)

(73) Assignee: Merck Patent GmbH, Darmstadt (DE)

( * ) Notice: Subject to any disclaimer, the term of this patent is extended or adjusted under 35 U.S.C. 154(b) by 93 days.

(21) Appl. No.: 10/468,026

(22) PCT Filed: Jan. 25, 2002

(86) PCT No.: PCT/EP02/00753

§ 371 (c)(1),
(2), (4) Date: Aug. 14, 2003

(87) PCT Pub. No.: WO02/066507

PCT Pub. Date: Aug. 29, 2002

(65) Prior Publication Data

US 2005/0070002 A1    Mar. 31, 2005

(30) Foreign Application Priority Data

Feb. 16, 2001 (EP) ................................. 01103779

(51) Int. Cl.
*C07K 1/00*    (2006.01)

(52) U.S. Cl. ..................................... 530/350; 435/69.1
(58) Field of Classification Search ................ 530/350; 435/69.1; 514/12
See application file for complete search history.

(56) References Cited

OTHER PUBLICATIONS

Pluvinet et al.: XP002224682, Oct. 1, 2000, abstract.
Pluvinet et al.: XP002224683, Jul. 1, 2000, abstract.
Ansorge W. et al.: XP002224684, Oct. 1, 2000, abstract.
Ansorge W. et al.: XP 002224685, Sep. 156, 1999, abstract.
Birren et al.: XP002224686, abstract.
Merck Patent GmbH: WO 00 52175 A, Sep. 8, 2000, SEQ ID Nos. 1, 2.
Luban J. et al.: "The Yeast Two-Hybrid System For Studying Protein-Protein Interactions", Current opinion in Biotechnology, London, GB, vol. 6, No. 1, 1995, pp. 59-64, XP000571534.

*Primary Examiner*—Karen Cochrane Carlson
*Assistant Examiner*—Agnes B. Rooke
(74) *Attorney, Agent, or Firm*—Millen, White, Zelano, Branigan, P.C

(57) ABSTRACT

PHPIP-120 polypeptides and polynucleotides and methods for producing such polypeptides by recombinant techniques are disclosed, also disclosed are methods for utilizing PHPIP-120 polypeptides and polynucleotides in diagnostic assays.

16 Claims, No Drawings

SEQUENCE LISTING

```
<160> NUMBER OF SEQ ID NOS: 8

<210> SEQ ID NO 1
<211> LENGTH: 3732
<212> TYPE: DNA
<213> ORGANISM: Homo sapiens
<220> FEATURE:
<221> NAME/KEY: CDS
```

-continued

<222> LOCATION: (184)..(3327)

<400> SEQUENCE: 1

| | | | | | | | | | | | | | | | | |
|---|---|---|---|---|---|---|---|---|---|---|---|---|---|---|---|---|
| ccgggcttgg tgctcactgc gacttcccgc gcagggcccg gtcggactag gacccgcggc | | | | | | | | | | | | | | | | 60 |
| ctgagagacg ctggaggatg cggacgcgga ggccgcctgg ggtagcggcg gcgggagtcc | | | | | | | | | | | | | | | | 120 |
| tggcgctctg caggtcagaa gttgagtagc aggggcctag gagggctcga agccttcaca | | | | | | | | | | | | | | | | 180 |

```
gcg  atg  gca  gag  aag  cga  ccc  ctg  aga  acc  ctg  ggg  cct  gtg  atg  tat      228
     Met  Ala  Glu  Lys  Arg  Pro  Leu  Arg  Thr  Leu  Gly  Pro  Val  Met  Tyr
      1                 5                        10                       15 ggc  aag  ctg  ccc  cgc  tta  gag  aca  gac  tcc  ggg  ctc  gag  cac  agc  ctg      276
Gly  Lys  Leu  Pro  Arg  Leu  Glu  Thr  Asp  Ser  Gly  Leu  Glu  His  Ser  Leu
                       20                       25                       30 ccc  cac  tct  gtt  ggt  aac  cag  gat  ccc  tgc  acc  tac  aag  ggg  tcc  tac      324
Pro  His  Ser  Val  Gly  Asn  Gln  Asp  Pro  Cys  Thr  Tyr  Lys  Gly  Ser  Tyr
                  35                       40                       45 ttc  tcc  tgc  ccc  atg  gca  ggt  act  cct  aag  gcc  gag  tct  gag  cag  ttg      372
Phe  Ser  Cys  Pro  Met  Ala  Gly  Thr  Pro  Lys  Ala  Glu  Ser  Glu  Gln  Leu
             50                       55                       60 gcg  tcc  tgg  acc  cca  tac  cca  ccc  ttg  tac  tct  acc  ggt  atg  gca  gga      420
Ala  Ser  Trp  Thr  Pro  Tyr  Pro  Pro  Leu  Tyr  Ser  Thr  Gly  Met  Ala  Gly
 65                       70                       75 ccc  cca  ctt  cag  gca  gac  aac  ctg  ctg  acc  aac  tgc  ctg  ttc  tac  cgc      468
Pro  Pro  Leu  Gln  Ala  Asp  Asn  Leu  Leu  Thr  Asn  Cys  Leu  Phe  Tyr  Arg
 80                       85                       90                       95 tcg  cca  gca  gaa  ggc  cct  gag  aag  atg  cag  gac  tcc  agc  cct  gtt  gag      516
Ser  Pro  Ala  Glu  Gly  Pro  Glu  Lys  Met  Gln  Asp  Ser  Ser  Pro  Val  Glu
                      100                      105                      110 ctc  ctg  ccc  ttc  agt  ccc  cag  gct  cac  tcc  tac  cca  ggc  cca  cca  ctg      564
Leu  Leu  Pro  Phe  Ser  Pro  Gln  Ala  His  Ser  Tyr  Pro  Gly  Pro  Pro  Leu
                 115                      120                      125 gca  gca  ccc  aaa  cct  gtc  tac  cgc  aac  cct  ctg  tgc  tat  ggg  ctc  tca      612
Ala  Ala  Pro  Lys  Pro  Val  Tyr  Arg  Asn  Pro  Leu  Cys  Tyr  Gly  Leu  Ser
            130                      135                      140 act  tgt  ctg  ggg  gaa  gga  gca  gtg  aag  agg  cca  ctg  gat  gtt  gac  tgg      660
Thr  Cys  Leu  Gly  Glu  Gly  Ala  Val  Lys  Arg  Pro  Leu  Asp  Val  Asp  Trp
      145                      150                      155 act  ctg  gcg  act  ggg  ccc  ctg  ttg  ccc  tca  gct  gac  cca  ccc  tgc  tct      708
Thr  Leu  Ala  Thr  Gly  Pro  Leu  Leu  Pro  Ser  Ala  Asp  Pro  Pro  Cys  Ser
160                      165                      170                      175 ctg  gcc  cca  gct  cct  agc  aag  ggc  cag  act  ctg  gat  ggc  acc  ttc  ttg      756
Leu  Ala  Pro  Ala  Pro  Ser  Lys  Gly  Gln  Thr  Leu  Asp  Gly  Thr  Phe  Leu
                 180                      185                      190 cgg  ggg  gtg  cca  gct  gag  ggg  tcc  agt  aaa  gac  tcc  tca  ggg  agc  ttc      804
Arg  Gly  Val  Pro  Ala  Glu  Gly  Ser  Ser  Lys  Asp  Ser  Ser  Gly  Ser  Phe
            195                      200                      205 tcc  cca  tgc  cag  ccc  ttc  ctg  gag  aaa  tat  cag  acc  atc  cac  agc  acg      852
Ser  Pro  Cys  Gln  Pro  Phe  Leu  Glu  Lys  Tyr  Gln  Thr  Ile  His  Ser  Thr
       210                      215                      220 ggc  ttc  ctg  gcc  tcc  agg  tac  aca  ggt  cct  tac  cct  agg  aac  tcc  aag      900
Gly  Phe  Leu  Ala  Ser  Arg  Tyr  Thr  Gly  Pro  Tyr  Pro  Arg  Asn  Ser  Lys
 225                      230                      235 caa  gca  atg  tct  gag  ggg  ccc  tca  agt  cct  tgg  acc  cag  ctg  gcc  cag      948
Gln  Ala  Met  Ser  Glu  Gly  Pro  Ser  Ser  Pro  Trp  Thr  Gln  Leu  Ala  Gln
240                      245                      250                      255 ccc  ctg  ggg  cca  ccc  tgt  cag  gac  acc  ggg  ccc  acc  cac  tac  cca  cca      996
Pro  Leu  Gly  Pro  Pro  Cys  Gln  Asp  Thr  Gly  Pro  Thr  His  Tyr  Pro  Pro
                 260                      265                      270 ccc  cac  cac  cca  cca  ccc  cac  cct  cca  cag  gcc  ctg  cct  tgc  cct  cca     1044
```

-continued

| | | |
|---|---|---|
| Pro His His Pro Pro His Pro Pro Gln Ala Leu Pro Cys Pro Pro<br>275                   280                  285 | | |
| gcc tgt cgc cac cca gag aag cag ggc agc tac agc cca gca ctc cca<br>Ala Cys Arg His Pro Glu Lys Gln Gly Ser Tyr Ser Pro Ala Leu Pro<br>        290                  295                  300 | 1092 | |
| ctg cag cct ctg ggg ggc cac aag ggg acc ggg tac cag gct ggt ggg<br>Leu Gln Pro Leu Gly Gly His Lys Gly Thr Gly Tyr Gln Ala Gly Gly<br>305                  310                  315 | 1140 | |
| ctg ggc agc ccc tac ctg agg cag cag gca gcc cag gca cct tac att<br>Leu Gly Ser Pro Tyr Leu Arg Gln Gln Ala Ala Gln Ala Pro Tyr Ile<br>320                  325                  330                  335 | 1188 | |
| ccc cca ctg ggg ctg gac gct tac ccc tac ccc tct gcc cct ctc cca<br>Pro Pro Leu Gly Leu Asp Ala Tyr Pro Tyr Pro Ser Ala Pro Leu Pro<br>              340                  345                  350 | 1236 | |
| gca ccc tct cca ggc ctc aag ctg gag ccg cct ctc act cca cgg tgc<br>Ala Pro Ser Pro Gly Leu Lys Leu Glu Pro Pro Leu Thr Pro Arg Cys<br>                  355                  360                  365 | 1284 | |
| cca ttg gac ttt gcc ccc cag aca ctg agt ttt cct tat gcc cgg gat<br>Pro Leu Asp Phe Ala Pro Gln Thr Leu Ser Phe Pro Tyr Ala Arg Asp<br>370                  375                  380 | 1332 | |
| gac ctc tct ctc tat gga gca tcc cct ggg ctt gga ggg aca cca cct<br>Asp Leu Ser Leu Tyr Gly Ala Ser Pro Gly Leu Gly Gly Thr Pro Pro<br>385                  390                  395 | 1380 | |
| tcc cag aac aat gtg cgg gct gtg cca cag cct ggt gcc ttc cag agg<br>Ser Gln Asn Asn Val Arg Ala Val Pro Gln Pro Gly Ala Phe Gln Arg<br>400                  405                  410                  415 | 1428 | |
| gca tgc cag cct ttg cca gcg agc cag ccc tgc tca gag cct gtg agg<br>Ala Cys Gln Pro Leu Pro Ala Ser Gln Pro Cys Ser Glu Pro Val Arg<br>              420                  425                  430 | 1476 | |
| cct gca cag gaa gcc gaa gag aag acc tgg ctg ccc agc tgc agg aaa<br>Pro Ala Gln Glu Ala Glu Glu Lys Thr Trp Leu Pro Ser Cys Arg Lys<br>                  435                  440                  445 | 1524 | |
| gag aag ctc cag ccc cgg ctc agt gag cac tct ggg ccg ccc atc gtc<br>Glu Lys Leu Gln Pro Arg Leu Ser Glu His Ser Gly Pro Pro Ile Val<br>450                  455                  460 | 1572 | |
| atc cga gac agt cca gtt ccc tgt acc ccc cca gca ctg ccc ccc tgt<br>Ile Arg Asp Ser Pro Val Pro Cys Thr Pro Pro Ala Leu Pro Pro Cys<br>465                  470                  475 | 1620 | |
| gcc cgg gag tgc cag tct ctt cca cag aag gag ggc gca agg cca ccc<br>Ala Arg Glu Cys Gln Ser Leu Pro Gln Lys Glu Gly Ala Arg Pro Pro<br>480                  485                  490                  495 | 1668 | |
| agc tct cca cca atg cct gtc att gac aat gtc ttc agc ctg gcc ccc<br>Ser Ser Pro Pro Met Pro Val Ile Asp Asn Val Phe Ser Leu Ala Pro<br>              500                  505                  510 | 1716 | |
| tac cgt gac tat ctg gat gtg ccg gca ccc gag gcc aca act gag cct<br>Tyr Arg Asp Tyr Leu Asp Val Pro Ala Pro Glu Ala Thr Thr Glu Pro<br>                  515                  520                  525 | 1764 | |
| gac tct gcc aca gct gag cct gac tca gcc cca gcc acc agt gaa ggt<br>Asp Ser Ala Thr Ala Glu Pro Asp Ser Ala Pro Ala Thr Ser Glu Gly<br>530                  535                  540 | 1812 | |
| cag gac aaa ggc tgc agg ggg acc ctg cct gcc cag gag ggc ccc tca<br>Gln Asp Lys Gly Cys Arg Gly Thr Leu Pro Ala Gln Glu Gly Pro Ser<br>545                  550                  555 | 1860 | |
| ggg agt aaa ccc cta agg ggc tca ctt aag gag gag gta gcc ctg gat<br>Gly Ser Lys Pro Leu Arg Gly Ser Leu Lys Glu Glu Val Ala Leu Asp<br>560                  565                  570                  575 | 1908 | |
| ttg agt gtg agg aag ccc aca gca gag gcc tcc cct gtc aag gct tcc<br>Leu Ser Val Arg Lys Pro Thr Ala Glu Ala Ser Pro Val Lys Ala Ser<br>              580                  585                  590 | 1956 | |

```
                                            -continued cgt tct gtg gag cat gcc aag cct act gca gcc atg gat gtg cca gat       2004
Arg Ser Val Glu His Ala Lys Pro Thr Ala Ala Met Asp Val Pro Asp
            595                 600                 605 gtg ggc aac atg gtg tca gat ctg cca ggc ctg aaa aag ata gac aca       2052
Val Gly Asn Met Val Ser Asp Leu Pro Gly Leu Lys Lys Ile Asp Thr
610                 615                 620 gaa gca cca ggc ttg cct ggg gtg cca gtg acc aca gat gcc atg cca       2100
Glu Ala Pro Gly Leu Pro Gly Val Pro Val Thr Thr Asp Ala Met Pro
    625                 630                 635 agg acc aac ttc cac agc tct gtg gcc ttc atg ttc cga aag ttc aag       2148
Arg Thr Asn Phe His Ser Ser Val Ala Phe Met Phe Arg Lys Phe Lys
640                 645                 650                 655 atc ctc cgt ccg gca cct ttg cct gca gcc gtg gtc ccg tcc acg ccc       2196
Ile Leu Arg Pro Ala Pro Leu Pro Ala Ala Val Val Pro Ser Thr Pro
                660                 665                 670 acc tca gct cct gct ccc aca cag cct gca ccc acc ccc aca tct ggg       2244
Thr Ser Ala Pro Ala Pro Thr Gln Pro Ala Pro Thr Pro Thr Ser Gly
            675                 680                 685 ccc att gga ctg cgg att ctc gct caa cag ccc ttg tct gtg acc tgc       2292
Pro Ile Gly Leu Arg Ile Leu Ala Gln Gln Pro Leu Ser Val Thr Cys
690                 695                 700 ttc agc ctg gca ctg ccc agc cct cca gcc gta gct gtg gcc tcc cct       2340
Phe Ser Leu Ala Leu Pro Ser Pro Pro Ala Val Ala Val Ala Ser Pro
705                 710                 715 gcc cct gct cca gct cca tcc cct gct ccg gct cga gct cag gct cca       2388
Ala Pro Ala Pro Ala Pro Ser Pro Ala Pro Ala Arg Ala Gln Ala Pro
720                 725                 730                 735 gct tca gcc cgg gat cca gct cca gct cca gtt gca ggc cct       2436
Ala Ser Ala Arg Asp Pro Ala Pro Ala Pro Val Ala Gly Pro
                740                 745                 750 gct cca gca tct act tca gcc cca ggg gac tcc ctg gag cag cat ttt       2484
Ala Pro Ala Ser Thr Ser Ala Pro Gly Asp Ser Leu Glu Gln His Phe
            755                 760                 765 aca gga cta cat gcg tcc ctg tgt gat gct att tct ggc tcc gtc gcc       2532
Thr Gly Leu His Ala Ser Leu Cys Asp Ala Ile Ser Gly Ser Val Ala
770                 775                 780 cac tct cct cca gag aag ctt cgc gag tgg cta gag acg gct ggg ccc       2580
His Ser Pro Pro Glu Lys Leu Arg Glu Trp Leu Glu Thr Ala Gly Pro
785                 790                 795 tgg ggc cag gct gcg tgg cag gac tgc cag ggt gtg cag ggg ctg ctg       2628
Trp Gly Gln Ala Ala Trp Gln Asp Cys Gln Gly Val Gln Gly Leu Leu
800                 805                 810                 815 gcc aag ctg ctg tct cag ctg cag cgc ttc gat cgc acc cac cgg tgc       2676
Ala Lys Leu Leu Ser Gln Leu Gln Arg Phe Asp Arg Thr His Arg Cys
                820                 825                 830 ccc ttc ccc cat gtg gtg cga gct ggc gcc atc ttc gtg ccc att cac       2724
Pro Phe Pro His Val Val Arg Ala Gly Ala Ile Phe Val Pro Ile His
            835                 840                 845 ctg gtg aag gag cgg ctc ttc cct cgg ctg cca ccc gct tct gtg gac       2772
Leu Val Lys Glu Arg Leu Phe Pro Arg Leu Pro Pro Ala Ser Val Asp
850                 855                 860 cat gtg ctg cag gag cat cgt gtg gag ctg cgg ccc acc acg ctg tcg       2820
His Val Leu Gln Glu His Arg Val Glu Leu Arg Pro Thr Thr Leu Ser
865                 870                 875 gag gag cgg gca ctg cgg gag ctc gcc ctg cca ggc tgc acc tca cgc       2868
Glu Glu Arg Ala Leu Arg Glu Leu Ala Leu Pro Gly Cys Thr Ser Arg
880                 885                 890                 895 atg ctg aag tta ctg gcg ctg cgc cag ctg ccg gac att tac ccc gac       2916
Met Leu Lys Leu Leu Ala Leu Arg Gln Leu Pro Asp Ile Tyr Pro Asp
                900                 905                 910
```

```
ctt ctc ggc ctg cag tgg cgc gac tgt gta cgc cgc cag ctg ggt gac     2964
Leu Leu Gly Leu Gln Trp Arg Asp Cys Val Arg Arg Gln Leu Gly Asp
            915                 920                 925 ttt gac act gag gct gga gct gtg tcc tcc tca gag ccc act gtg gcc     3012
Phe Asp Thr Glu Ala Gly Ala Val Ser Ser Ser Glu Pro Thr Val Ala
        930                 935                 940 aga ggt gag cca gag agc cta gcc ctg gct cag aag tca ccg gcc ccc     3060
Arg Gly Glu Pro Glu Ser Leu Ala Leu Ala Gln Lys Ser Pro Ala Pro
    945                 950                 955 aag gtc agg aag cca ggc agg aag cca cca acc cct ggc ccg gag aaa     3108
Lys Val Arg Lys Pro Gly Arg Lys Pro Pro Thr Pro Gly Pro Glu Lys
960                 965                 970                 975 gca gag gca gct gct ggg gaa gag tcc tgt ggt gcc tcc cct acc cct     3156
Ala Glu Ala Ala Ala Gly Glu Glu Ser Cys Gly Ala Ser Pro Thr Pro
                980                 985                 990 gct acc agt gcc agc cca cct ggc ccc aca ctg aag gcc cgc ttc cgc     3204
Ala Thr Ser Ala Ser Pro Pro Gly Pro Thr Leu Lys Ala Arg Phe Arg
            995                 1000                1005 agt ctg ctg gag acc gcc tgg ctc aat ggc ctg gct ctg ccc acc tgg     3252
Ser Leu Leu Glu Thr Ala Trp Leu Asn Gly Leu Ala Leu Pro Thr Trp
        1010                1015                1020 ggc cac aag tcc tca aga cca gac cag ccc tca ccc tgc cca cag ctg     3300
Gly His Lys Ser Ser Arg Pro Asp Gln Pro Ser Pro Cys Pro Gln Leu
    1025                1030                1035 ctg gac agc cag agc cat cac ctg tag cactggttgc cagtgctgtg          3347
Leu Asp Ser Gln Ser His His Leu
1040                1045 tgtatagcag tcactctcca cccttccctt ctgcctgccc agctgccccg gggccacgag  3407
tggatgctgg ggctgtggct gctccccctgg aggggttcca tctctgaccc tgtgccccat 3467 tcagggtggg ctgaagagcc cctgagcttt taacgtgagg gtctttattg gataggacta  3527 ctccctatttt cttgcctaga gaacacacat gggctttgga gcccgacaga cctgggcttg 3587 aatcccggct cgtgttcttg ctgcaggacc tgggcaagaa acttcacctc tgctgagccc  3647
tcattcccca tgtgtaaaat gggacaacgc aacctacctc acagggttgt tgtggggatg  3707
ctgcctgata catacccctgt cacca                                       3732

<210> SEQ ID NO 2
<211> LENGTH: 1047
<212> TYPE: PRT
<213> ORGANISM: Homo sapiens

<400> SEQUENCE: 2

Met Ala Glu Lys Arg Pro Leu Arg Thr Leu Gly Pro Val Met Tyr Gly
1               5                   10                  15

Lys Leu Pro Arg Leu Glu Thr Asp Ser Gly Leu Glu His Ser Leu Pro
            20                  25                  30

His Ser Val Gly Asn Gln Asp Pro Cys Thr Tyr Lys Gly Ser Tyr Phe
        35                  40                  45

Ser Cys Pro Met Ala Gly Thr Pro Lys Ala Glu Ser Glu Gln Leu Ala
    50                  55                  60

Ser Trp Thr Pro Tyr Pro Pro Leu Tyr Ser Thr Gly Met Ala Gly Pro
65                  70                  75                  80

Pro Leu Gln Ala Asp Asn Leu Leu Thr Asn Cys Leu Phe Tyr Arg Ser
                85                  90                  95

Pro Ala Glu Gly Pro Glu Lys Met Gln Asp Ser Ser Pro Val Glu Leu
            100                 105                 110
```

```
Leu Pro Phe Ser Pro Gln Ala His Ser Tyr Pro Gly Pro Pro Leu Ala
            115                 120                 125
Ala Pro Lys Pro Val Tyr Arg Asn Pro Leu Cys Tyr Gly Leu Ser Thr
        130                 135                 140
Cys Leu Gly Glu Gly Ala Val Lys Arg Pro Leu Asp Val Asp Trp Thr
145                 150                 155                 160
Leu Ala Thr Gly Pro Leu Leu Pro Ser Ala Asp Pro Cys Ser Leu
                165                 170                 175
Ala Pro Ala Pro Ser Lys Gly Gln Thr Leu Asp Gly Thr Phe Leu Arg
            180                 185                 190
Gly Val Pro Ala Glu Gly Ser Ser Lys Asp Ser Ser Gly Ser Phe Ser
        195                 200                 205
Pro Cys Gln Pro Phe Leu Glu Lys Tyr Gln Thr Ile His Ser Thr Gly
    210                 215                 220
Phe Leu Ala Ser Arg Tyr Thr Gly Pro Tyr Pro Arg Asn Ser Lys Gln
225                 230                 235                 240
Ala Met Ser Glu Gly Pro Ser Ser Pro Trp Thr Gln Leu Ala Gln Pro
            245                 250                 255
Leu Gly Pro Pro Cys Gln Asp Thr Gly Pro Thr His Tyr Pro Pro Pro
            260                 265                 270
His His Pro Pro His Pro Pro Gln Ala Leu Pro Cys Pro Pro Ala
    275                 280                 285
Cys Arg His Pro Glu Lys Gln Gly Ser Tyr Ser Pro Ala Leu Pro Leu
    290                 295                 300
Gln Pro Leu Gly Gly His Lys Gly Thr Gly Tyr Gln Ala Gly Gly Leu
305                 310                 315                 320
Gly Ser Pro Tyr Leu Arg Gln Gln Ala Ala Gln Ala Pro Tyr Ile Pro
                325                 330                 335
Pro Leu Gly Leu Asp Ala Tyr Pro Tyr Pro Ser Ala Pro Leu Pro Ala
                340                 345                 350
Pro Ser Pro Gly Leu Lys Leu Glu Pro Pro Leu Thr Pro Arg Cys Pro
            355                 360                 365
Leu Asp Phe Ala Pro Gln Thr Leu Ser Phe Pro Tyr Ala Arg Asp Asp
    370                 375                 380
Leu Ser Leu Tyr Gly Ala Ser Pro Gly Leu Gly Gly Thr Pro Pro Ser
385                 390                 395                 400
Gln Asn Asn Val Arg Ala Val Pro Gln Pro Gly Ala Phe Gln Arg Ala
                405                 410                 415
Cys Gln Pro Leu Pro Ala Ser Gln Pro Cys Ser Glu Pro Val Arg Pro
            420                 425                 430
Ala Gln Glu Ala Glu Lys Thr Trp Leu Pro Ser Cys Arg Lys Glu
        435                 440                 445
Lys Leu Gln Pro Arg Leu Ser Glu His Ser Gly Pro Pro Ile Val Ile
    450                 455                 460
Arg Asp Ser Pro Val Pro Cys Thr Pro Ala Leu Pro Pro Cys Ala
465                 470                 475                 480
Arg Glu Cys Gln Ser Leu Pro Gln Lys Glu Gly Ala Arg Pro Pro Ser
                485                 490                 495
Ser Pro Pro Met Pro Val Ile Asp Asn Val Phe Ser Leu Ala Pro Tyr
            500                 505                 510
Arg Asp Tyr Leu Asp Val Pro Ala Pro Glu Ala Thr Thr Glu Pro Asp
    515                 520                 525
```

```
Ser Ala Thr Ala Glu Pro Asp Ser Ala Pro Ala Thr Ser Glu Gly Gln
    530                 535                 540

Asp Lys Gly Cys Arg Gly Thr Leu Pro Ala Gln Glu Gly Pro Ser Gly
545                 550                 555                 560

Ser Lys Pro Leu Arg Gly Ser Leu Lys Glu Glu Val Ala Leu Asp Leu
                565                 570                 575

Ser Val Arg Lys Pro Thr Ala Glu Ala Ser Pro Val Lys Ala Ser Arg
            580                 585                 590

Ser Val Glu His Ala Lys Pro Thr Ala Ala Met Asp Val Pro Asp Val
        595                 600                 605

Gly Asn Met Val Ser Asp Leu Pro Gly Leu Lys Lys Ile Asp Thr Glu
    610                 615                 620

Ala Pro Gly Leu Pro Gly Val Pro Val Thr Thr Asp Ala Met Pro Arg
625                 630                 635                 640

Thr Asn Phe His Ser Ser Val Ala Phe Met Phe Arg Lys Phe Lys Ile
                645                 650                 655

Leu Arg Pro Ala Pro Leu Pro Ala Ala Val Pro Ser Thr Pro Thr
            660                 665                 670

Ser Ala Pro Ala Pro Thr Gln Pro Ala Pro Thr Pro Thr Ser Gly Pro
        675                 680                 685

Ile Gly Leu Arg Ile Leu Ala Gln Gln Pro Leu Ser Val Thr Cys Phe
    690                 695                 700

Ser Leu Ala Leu Pro Ser Pro Pro Ala Val Ala Val Ala Ser Pro Ala
705                 710                 715                 720

Pro Ala Pro Ala Pro Ser Pro Ala Pro Ala Arg Ala Gln Ala Pro Ala
                725                 730                 735

Ser Ala Arg Asp Pro Ala Pro Ala Pro Ala Pro Val Ala Gly Pro Ala
            740                 745                 750

Pro Ala Ser Thr Ser Ala Pro Gly Asp Ser Leu Glu Gln His Phe Thr
        755                 760                 765

Gly Leu His Ala Ser Leu Cys Asp Ala Ile Ser Gly Ser Val Ala His
    770                 775                 780

Ser Pro Pro Glu Lys Leu Arg Glu Trp Leu Glu Thr Ala Gly Pro Trp
785                 790                 795                 800

Gly Gln Ala Ala Trp Gln Asp Cys Gln Gly Val Gln Gly Leu Leu Ala
                805                 810                 815

Lys Leu Leu Ser Gln Leu Gln Arg Phe Asp Arg Thr His Arg Cys Pro
            820                 825                 830

Phe Pro His Val Val Arg Ala Gly Ala Ile Phe Val Pro Ile His Leu
        835                 840                 845

Val Lys Glu Arg Leu Phe Pro Arg Leu Pro Ala Ser Val Asp His
    850                 855                 860

Val Leu Gln Glu His Arg Val Glu Leu Arg Pro Thr Thr Leu Ser Glu
865                 870                 875                 880

Glu Arg Ala Leu Arg Glu Leu Ala Leu Pro Gly Cys Thr Ser Arg Met
                885                 890                 895

Leu Lys Leu Leu Ala Leu Arg Gln Leu Pro Asp Ile Tyr Pro Asp Leu
            900                 905                 910

Leu Gly Leu Gln Trp Arg Asp Cys Val Arg Arg Gln Leu Gly Asp Phe
        915                 920                 925

Asp Thr Glu Ala Gly Ala Val Ser Ser Glu Pro Thr Val Ala Arg
    930                 935                 940

Gly Glu Pro Glu Ser Leu Ala Leu Ala Gln Lys Ser Pro Ala Pro Lys
```

-continued

```
                945                 950                 955                 960
Val Arg Lys Pro Gly Arg Lys Pro Pro Thr Pro Gly Pro Glu Lys Ala
                    965                 970                 975
Glu Ala Ala Ala Gly Glu Glu Ser Cys Gly Ala Ser Pro Thr Pro Ala
                980                 985                 990
Thr Ser Ala Ser Pro Pro Gly Pro Thr Leu Lys Ala Arg Phe Arg Ser
            995                1000                1005
Leu Leu Glu Thr Ala Trp Leu Asn Gly Leu Ala Leu Pro Thr Trp Gly
   1010                1015                1020
His Lys Ser Ser Arg Pro Asp Gln Pro Ser Pro Cys Pro Gln Leu Leu
1025                1030                1035                1040
Asp Ser Gln Ser His His Leu
            1045

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Primer 1

<400> SEQUENCE: 3
ttttgtcgac catggcggtg gcggacctcg                                    30

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Primer 2

<400> SEQUENCE: 4
ttttgcggcc gctcagtagc cgtcgttagc c                                  31

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Primer 3

<400> SEQUENCE: 5
aattccaggt cgacctcgag gcggccgct                                     29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Primer 4

<400> SEQUENCE: 6
tcgaaccggc cgcctcgagg tcgacctgg                                     29

<210> SEQ ID NO 7
<211> LENGTH: 276
<212> TYPE: PRT
<213> ORGANISM: Artificial Sequence
<220> FEATURE:
<223> OTHER INFORMATION: Description of Artificial Sequence:
      Fusionprotein Gal4-PHP1

<400> SEQUENCE: 7
```

```
Met Lys Leu Leu Ser Ser Ile Glu Gln Ala Cys Asp Ile Cys Arg Leu
 1               5                  10                  15

Lys Lys Leu Lys Cys Ser Lys Glu Lys Pro Lys Cys Ala Lys Cys Leu
                20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
        50                  55                  60

Glu Gln Leu Phe Leu Leu Ile Phe Pro Arg Glu Asp Leu Asp Met Ile
 65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
                100                 105                 110

Ser Val Glu Thr Asp Met Pro Leu Thr Leu Arg Gln His Arg Ile Ser
                115                 120                 125

Ala Thr Ser Ser Ser Glu Gly Ser Ser Asn Lys Gly Gln Arg Gln Leu
        130                 135                 140

Thr Val Ser Ser Arg Ser Thr Met Ala Val Ala Asp Leu Ala Leu Ile
145                 150                 155                 160

Pro Asp Val Asp Ile Asp Ser Asp Gly Val Phe Lys Tyr Val Leu Ile
                165                 170                 175

Arg Val His Ser Ala Pro Arg Ser Gly Ala Pro Ala Ala Glu Ser Lys
                180                 185                 190

Glu Ile Val Arg Gly Tyr Lys Trp Ala Glu Tyr His Ala Asp Ile Tyr
                195                 200                 205

Asp Lys Val Ser Gly Asp Met Gln Lys Gln Gly Cys Asp Cys Glu Cys
210                 215                 220

Leu Gly Gly Gly Arg Ile Ser His Gln Ser Gln Asp Lys Lys Ile His
225                 230                 235                 240

Val Tyr Gly Tyr Ser Met Ala Tyr Gly Pro Ala Gln His Ala Ile Ser
                245                 250                 255

Thr Glu Lys Ile Lys Ala Lys Tyr Pro Asp Tyr Glu Val Thr Trp Ala
                260                 265                 270

Asn Asp Gly Tyr
            275

<210> SEQ ID NO 8
<211> LENGTH: 332
<212> TYPE: PRT
<213> ORGANISM: Artificial Sequence
<220> FEATURE:
<223> OTHER INFORMATION: Description of Artificial Sequence:
      Fusionprotein LexA-PHP1

<400> SEQUENCE: 8

Met Lys Ala Leu Thr Ala Arg Gln Gln Glu Val Phe Asp Leu Ile Arg
 1               5                  10                  15

Asp His Ile Ser Gln Thr Gly Met Pro Pro Thr Arg Ala Glu Ile Ala
                20                  25                  30

Gln Arg Leu Gly Phe Arg Ser Pro Asn Ala Ala Glu Glu His Leu Lys
            35                  40                  45

Ala Leu Ala Arg Lys Gly Val Ile Glu Ile Val Ser Gly Ala Ser Arg
        50                  55                  60

Gly Ile Arg Leu Leu Gln Glu Glu Glu Glu Gly Leu Pro Leu Val Gly
 65                  70                  75                  80
```

-continued

```
Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
               100                 105                 110

Leu Arg Val Ser Gly Met Ser Met Lys Asp Ile Gly Ile Met Asp Gly
           115                 120                 125

Asp Leu Leu Ala Val His Lys Thr Gln Asp Val Arg Asn Gly Gln Val
       130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
               165                 170                 175

Ile Val Val Asp Leu Arg Gln Gln Ser Phe Thr Ile Glu Gly Leu Ala
               180                 185                 190

Val Gly Val Ile Arg Asn Gly Asp Trp Leu Glu Phe Arg Ser Thr Met
           195                 200                 205

Ala Val Ala Asp Leu Ala Leu Ile Pro Asp Val Asp Ile Asp Ser Asp
       210                 215                 220

Gly Val Phe Lys Tyr Val Leu Ile Arg Val His Ser Ala Pro Arg Ser
225                 230                 235                 240

Gly Ala Pro Ala Ala Glu Ser Lys Glu Ile Val Arg Gly Tyr Lys Trp
               245                 250                 255

Ala Glu Tyr His Ala Asp Ile Tyr Asp Lys Val Ser Gly Asp Met Gln
               260                 265                 270

Lys Gln Gly Cys Asp Cys Glu Cys Leu Gly Gly Arg Ile Ser His
           275                 280                 285

Gln Ser Gln Asp Lys Lys Ile His Val Tyr Gly Tyr Ser Met Ala Tyr
       290                 295                 300

Gly Pro Ala Gln His Ala Ile Ser Thr Glu Lys Ile Lys Ala Lys Tyr
305                 310                 315                 320

Pro Asp Tyr Glu Val Thr Trp Ala Asn Asp Gly Tyr
               325                 330
```

HISTIDINE PHOSPHATASE INTERACTING PROTEIN WITH 120KD

This application is a 371 of PCT/EP02/00753 filed on Jan. 25, 2005, which claims foreign priority to EUROPEAN PATENT OFFICE (EPO) 01103779.3 filed on Feb. 16, 2001.

FIELD OF THE INVENTION

This invention relates to newly identified polypeptides and polynucleotides encoding such polypeptides sometimes hereinafter referred to as "novel Protein Histidine Phosphatase Interacting Partner of 120 kD (PHPIP-120)", to their use in diagnosis and in identifying compounds that may be agonists, antagonists that are potentially useful in therapy, and to production of such polypeptides and polynucleotides.

BACKGROUND OF THE INVENTION

Functional genomics relies heavily on high-throughput and the various tools of bioinformatics to identify gene sequences of potential interest from the many molecular biology databases now available. There is a continuing need to identify and characterise further genes and their related polypeptides/proteins, as targets for drug discovery.

Recently, the first human protein histidine phosphatase (PHP1) has been identified. The enzyme was isolated from rabbit liver extracts and characterized. In human cell lines PHP1 is displayed in the cytoplasma. Functional studies with the orthologue protein in C. elegans showed a neuronal localization. The C. elegans homologue of PHP1 has been localized in motor- and pharyngeal sensorineurons MC, M3 and I2. The analogy from a nematode's pharynx to the human heart is described (PNAS 1998 95, 5072–5) thus, PHP1 and ligand could be relevant for various cardiovascular diseases.

In the current application protein interaction studies with PHP1 have been used in combination with DNA sequencing technologies and bioinformatics to identify gene sequences and gene functions that are ligands and interaction partners of PHP-1 on a molecular level.

SUMMARY OF THE INVENTION

Protein interaction studies with PHP1 identified the PHPIP-120 as a yet unknown interaction partners.

The present invention relates to PHPIP-120, in particular PHPIP-120 polypeptides and PHPIP-120 polynucleotides, recombinant materials and methods for their production. Such polypeptides and polynucleotides are of interest in relation to methods of treatment of certain diseases, including, but not limited to autismus: a defect in nerve cells membrane activity linked to the fatty acid metabolim (Am J Med Genet. 2000 Dec. 4;96(6):765–70), schizophrenia (Psychiatr Q 1994 Winter; 65(4):287–97), familial recurrent arthritis (Arthritis Rheum 2000 September; 43(9):2041–5), Bardet-Biedl Syndrome (BBS4) (Genomics 1997 Apr. 1; 41(1):93–9), congenital dyserythropoietic anemia type III (Haematologica 2000 85,753–7), and Malignant fibrous histocytomas where comparative genomic hybridization (CGH) profiles identified chromosome 15q22-q26 as well as the locus of PHPIP-240 chromosome 13q32-q34 as the most frequent imbalance in this tissue sarcoma (Cancer Genet Cytogenet 1999; 111, 134–8) hereinafter referred to as "diseases of the invention". In a further aspect, the invention relates to methods for identifying agonists and antagonists (e.g., inhibitors) using the materials provided by the invention, and treating conditions associated with PHPIP-120 imbalance with the identified compounds. In a still further aspect, the invention relates to diagnostic assays for detecting diseases associated with inappropriate PHPIP-120 activity or levels.

DESCRIPTION OF THE INVENTION

In a first aspect, the present invention relates to PHPIP-120 polypeptides. Such polypeptides include:

(a) an isolated polypeptide encoded by a polynucleotide comprising the sequence of SEQ ID NO:1;

(b) an isolated polypeptide comprising a polypeptide sequence having at least 95%, 96%, 97%, 98%, or 99% identity to the polypeptide sequence of SEQ ID NO:2;

(c) an isolated polypeptide comprising the polypeptide sequence of SEQ ID NO:2;

(d) an isolated polypeptide having at least 95%, 96%, 97%, 98%, or 99% identity to the polypeptide sequence of SEQ ID NO:2;

(e) the polypeptide sequence of SEQ ID NO:2; and (f) an isolated polypeptide having or comprising a polypeptide sequence that has an Identity Index of 0.95, 0.96, 0.97, 0.98, or 0.99 compared to the polypeptide sequence of SEQ ID NO:2;

(g) fragments and variants of such polypeptides in (a) to (f).

Polypeptides of the present invention are members of the PHPIP-120 family of polypeptides. PHPIP-120 is therefore of interest because they are ligands for human protein histidine phosphatase (PHP1). Hisitidine phosphorylation in mammals is involved in signal transduction via multimeric protein complexes. In human cell lines PHP1 is displayed in the cytoplasma of cells with neuronal localization, however other cell types outside that location do express it as well. Thus the new ligand is relevant for other diseases and especially for various cardiovascular disorders.

The biological properties of the PHPIP-120 are hereinafter referred to as "biological activity of PHPIP-120" or "PHPIP-120 activity". Preferably, a polypeptide of the present invention exhibits at least one biological activity of PHPIP-120.

Polypeptides of the present invention also includes variants of the aforementioned polypeptides, including all allelic forms and splice variants. Such polypeptides vary from the reference polypeptide by insertions, deletions, and substitutions that may be conservative or non-conservative, or any combination thereof. Particularly preferred variants are those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination.

Preferred fragments of polypeptides of the present invention include an isolated polypeptide comprising an amino acid sequence having at least 30, 50 or 100 contiguous amino acids from the amino acid sequence of SEQ ID NO: 2, or an isolated polypeptide comprising an amino acid sequence having at least 30, 50 or 100 contiguous amino acids truncated or deleted from the amino acid sequence of SEQ ID NO: 2. Preferred fragments are biologically active fragments that mediate the biological activity of PHPIP-120, including those with a similar activity or an improved activity, or with a decreased undesirable activity. Also preferred are those fragments that are antigenic or immunogenic in an animal, especially in a human.

Fragments of the polypeptides of the invention may be employed for producing the corresponding full-length polypeptide by peptide synthesis; therefore, these variants may be employed as intermediates for producing the full-length polypeptides of the invention. The polypeptides of the present invention may be in the form of the "mature" protein or may be a part of a larger protein such as a precursor or a fusion protein. It is often advantageous to include an additional amino acid sequence that contains secretory or leader sequences, pro-sequences, sequences that aid in purification, for instance multiple histidine residues, or an additional sequence for stability during recombinant production.

Polypeptides of the present invention can be prepared in any suitable manner, for instance by isolation form naturally occurring sources, from genetically engineered host cells comprising expression systems (vide infra) or by chemical synthesis, using for instance automated peptide synthesizers, or a combination of such methods. Means for preparing such polypeptides are well understood in the art.

In a further aspect, the present invention relates to PHPIP-120 polynucleotides. Such polynucleotides include:
(a) an isolated polynucleotide comprising a polynucleotide sequence having at least 95%, 96%, 97%, 98%, or 99% identity to the polynucleotide sequence of SEQ ID NO:1;
(b) an isolated polynucleotide comprising the polynucleotide of SEQ ID NO:1;
(c) an isolated polynucleotide having at least 95%, 96%, 97%, 98%, or 99% identity to the polynucleotide of SEQ ID NO:1;
(d) the isolated polynucleotide of SEQ ID NO:1;
(e) an isolated polynucleotide comprising a polynucleotide sequence encoding a polypeptide sequence having at least 95%, 96%, 97%, 98%, or 99% identity to the polypeptide sequence of SEQ ID NO:2;
(f) an isolated polynucleotide comprising a polynucleotide sequence encoding the polypeptide of SEQ ID NO:2;
(g) an isolated polynucleotide having a polynucleotide sequence encoding a polypeptide sequence having at least 95%, 96%, 97%, 98%, or 99% identity to the polypeptide sequence of SEQ ID NO:2;
(h) an isolated polynucleotide encoding the polypeptide of SEQ ID NO:2;
(i) an isolated polynucleotide having or comprising a polynucleotide sequence that has an Identity Index of 0.95, 0.96, 0.97, 0.98, or 0.99 compared to the polynucleotide sequence of SEQ ID NO:1;
(j) an isolated polynucleotide having or comprising a polynucleotide sequence encoding a polypeptide sequence that has an Identity Index of 0.95, 0.96, 0.97, 0.98, or 0.99 compared to the polypeptide sequence of SEQ ID NO:2; and polynucleotides that are fragments and variants of the above mentioned polynucleotides or that are complementary to above mentioned polynucleotides, over the entire length thereof.

Preferred fragments of polynucleotides of the present invention include an isolated polynucleotide comprising an nucleotide sequence having at least 15, 30, 50 or 100 contiguous nucleotides from the sequence of SEQ ID NO: 1, or an isolated polynucleotide comprising an sequence having at least 30, 50 or 100 contiguous nucleotides truncated or deleted from the sequence of SEQ ID NO: 1.

Preferred variants of polynucleotides of the present invention include splice variants, allelic variants, and polymorphisms, including polynucleotides having one or more single nucleotide polymorphisms (SNPs).

Polynucleotides of the present invention also include polynucleotides encoding polypeptide variants that comprise the amino acid sequence of SEQ ID NO:2 and in which several, for instance from 50 to 30, from 30 to 20, from 20 to 10, from 10 to 5, from 5 to 3, from 3 to 2, from 2 to 1 or 1 amino acid residues are substituted, deleted or added, in any combination.

In a further aspect, the present invention provides polynucleotides that are RNA transcripts of the DNA sequences of the present invention. Accordingly, there is provided an RNA polynucleotide that:
(a) comprises an RNA transcript of the DNA sequence encoding the polypeptide of SEQ ID NO:2;
(b) is the RNA transcript of the DNA sequence encoding the polypeptide of SEQ ID NO:2;
(c) comprises an RNA transcript of the DNA sequence of SEQ ID NO:1; or
(d) is the RNA transcript of the DNA sequence of SEQ ID NO:1;

and RNA polynucleotides that are complementary thereto.

The polynucleotide sequence of SEQ ID NO:1 is a cDNA sequence that encodes the polypeptide of SEQ ID NO:2. The polynucleotide sequence encoding the polypeptide of SEQ ID NO:2 may be identical to the polypeptide encoding sequence of SEQ ID NO:1 or it may be a sequence other than SEQ ID NO:1, which, as a result of the redundancy (degeneracy) of the genetic code, also encodes the polypeptide of SEQ ID NO:2.

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one PHPIP-120 activity.

Polynucleotides of the present invention may be obtained using standard cloning and screening techniques from a cDNA library derived from mRNA in cells of heart, skeletal muscle, liver, kidney, brain. However PHP1 might as well be isolated from other human tissues, where lower levels are found. The substrate specificity identifies a role in the biosynthesis of fatty acids via preparation of acetylCoA. Accordingly, the biosynthesis of acetylcholine is regulated in nerve cells.

(see for instance, Sambrook et al., Molecular Cloning: A Laboratory Manual, 2nd Ed., Cold Spring Harbor Laboratory Press, Cold Spring Harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro-protein sequence, or other fusion peptide portions. For example, a marker sequence that facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Polynucleotides that are identical, or have sufficient identity to a polynucleotide sequence of SEQ ID NO:1, may be used as hybridization probes for cDNA and genomic DNA or as primers for a nucleic acid amplification reaction (for instance, PCR). Such probes and primers may be used to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1, typically at least 95% identity. Preferred probes and primers will generally comprise at least 15 nucleotides, preferably, at least 30 nucleotides and may have at least 50, if not at least 100 nucleotides. Particularly preferred probes will have between 30 and 50 nucleotides. Particularly preferred primers will have between 20 and 25 nucleotides.

A polynucleotide encoding a polypeptide of the present invention, including homologs from species other than human, may be obtained by a process comprising the steps of screening a library under stringent hybridization conditions with a labeled probe having the sequence of SEQ ID NO: 1 or a fragment thereof, preferably of at least 15 nucleotides; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 microgram/ml denatured, sheared salmon sperm DNA; followed by washing the filters in 0.1×SSC at about 65° C. Thus the present invention also includes isolated polynucleotides, preferably with a nucleotide sequence of at least 100, obtained by screening a library under stringent hybridization conditions with a labeled probe having the sequence of SEQ ID NO:1 or a fragment thereof, preferably of at least 15 nucleotides.

The skilled artisan will appreciate that, in many cases, an isolated cDNA sequence will be incomplete, in that the region coding for the polypeptide does not extend all the way through to the 5' terminus. This is a consequence of reverse transcriptase, an enzyme with inherently low "processivity" (a measure of the ability of the enzyme to remain attached to the template during the polymerisation reaction), failing to complete a DNA copy of the mRNA template during first strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., Proc Nat Acad Sci USA 85, 8998–9002, 1988). Recent modifications of the technique, exemplified by the Marathon (trade mark) technology (Clontech Laboratories Inc.) for example, have significantly simplified the search for longer cDNAs. In the Marathon (trade mark) technology, cDNAs have been prepared from mRNA extracted from a chosen tissue and an 'adaptor' sequence ligated onto each end. Nucleic acid amplification (PCR) is then carried out to amplify the "missing" 5' end of the cDNA using a combination of gene specific and adaptor specific oligonucleotide primers. The PCR reaction is then repeated using 'nested' primers, that is, primers designed to anneal within the amplified product (typically an adapter specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems comprising a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Polynucleotides may be introduced into host cells by methods described in many standard laboratory manuals, such as Davis et al., Basic Methods in Molecular Biology (1986) and Sambrook et al.(ibid). Preferred methods of introducing polynucleotides into host cells include, for instance, calcium phosphate transfection, DEAE-dextran mediated transfection, transvection, micro-injection, cationic lipid-mediated transfection, electroporation, transduction, scrape loading, ballistic introduction or infection.

Representative examples of appropriate hosts include bacterial cells, such as Streptococci, Staphylococci, *E. coli*, *Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector that is able to maintain, propagate or express a polynucleotide to produce a polypeptide in a host may be used. The appropriate polynucleotide sequence may be inserted into an expression system by any of a variety of well-known and routine techniques, such as, for example, those set forth in Sambrook et al., (ibid). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during intracellular synthesis, isolation and/or purification.

Polynucleotides of the present invention may be used as diagnostic reagents, through detecting mutations in the associated gene. Detection of a mutated form of the gene characterized by the polynucleotide of SEQ ID NO:1 in the cDNA or genomic sequence and which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques well known in the art.

Nucleic acids for diagnosis may be obtained from a subject's cells, such as from blood, urine, saliva, tissue biopsy or autopsy material. The genomic DNA may be used directly for detection or it may be amplified enzymatically by using PCR, preferably RT-PCR, or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled PHPIP-120 nucleotide sequences. Perfectly matched sequences can be distinguished from mismatched duplexes by RNase digestion or by differences in melting temperatures. DNA sequence difference may also be detected by alterations in the electrophoretic mobility of DNA fragments in gels, with or without denaturing agents, or by direct DNA sequencing (see, for instance, Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401).

An array of oligonucleotides probes comprising PHPIP-120 polynucleotide sequence or fragments thereof can be constructed to conduct efficient screening of e.g., genetic mutations. Such arrays are preferably high density arrays or grids. Array technology methods are well known and have general applicability and can be used to address a variety of questions in molecular genetics including gene expression, genetic linkage, and genetic variability, see, for example, M. Chee et al., Science, 274, 610–613 (1996) and other references cited therein.

Detection of abnormally decreased or increased levels of polypeptide or mRNA expression may also be used for diagnosing or determining susceptibility of a subject to a disease of the invention. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radio-immunoassays, competitive-binding assays, Western Blot analysis and ELISA assays.

Thus in another aspect, the present invention relates to a diagnostic kit comprising:
  (a) a polynucleotide of the present invention, preferably the nucleotide sequence of SEQ ID NO: 1, or a fragment or an RNA transcript thereof;
  (b) a nucleotide sequence complementary to that of (a);
  (c) a polypeptide of the present invention, preferably the polypeptide of SEQ ID NO:2 or a fragment thereof; or
  (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a disease, particularly diseases of the invention, amongst others.

The polynucleotide sequences of the present invention are valuable for chromosome localisation studies. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (co-inheritance of physically adjacent genes). Precise human chromosomal localisations for a genomic sequence (gene fragment etc.) can be determined using Radiation Hybrid (RH) Mapping (Walter, M. Spillett, D., Thomas, P., Weissenbach, J., and Goodfellow, P., (1994) A method for constructing radiation hybrid maps of whole genomes, Nature Genetics 7, 22–28). A number of RH panels are available from Research Genetics (Huntsville, Ala., USA) e.g. the GeneBridge4 RH panel (Hum Mol Genet 1996 March; 5(3):339–46 A radiation hybrid map of the human genome. Gyapay G, Schmitt K, Fizames C, Jones H, Vega-Czarny N, Spillett D, Muselet D, Prud'Homme J F, Dib C, Auffray C, Morissette J, Weissenbach J, Goodfellow P N). To determine the chromosomal location of a gene using this panel, 93 PCRs are performed using primers designed from the gene of interest on RH DNAs. Each of these DNAs contains random human genomic fragments maintained in a hamster background (human/hamster hybrid cell lines). These PCRs result in 93 scores indicating the presence or absence of the PCR product of the gene of interest. These scores are compared with scores created using PCR products from genomic sequences of known location. This comparison is conducted at http://www.genome.wi.mit.edu/. The gene of the present invention maps to human chromosome 15q22-q23.

The polynucleotide sequences of the present invention are also valuable tools for tissue expression studies. Such studies allow the determination of expression patterns of polynucleotides of the present invention which may give an indication as to the expression patterns of the encoded polypeptides in tissues, by detecting the mRNAs that encode them. The techniques used are well known in the art and include in situ hydridization techniques to clones arrayed on a grid, such as cDNA microarray hybridization (Schena et al, Science, 270, 467–470, 1995 and Shalon et al, Genome Res, 6, 639–445, 1996) and nucleotide amplification techniques such as PCR. A preferred method uses the TAQMAN (Trade mark) technology available from Perkin Elmer. Results from these studies can provide an indication of the normal function of the polypeptide in the organism. In addition, comparative studies of the normal expression pattern of mRNAs with that of mRNAs encoded by an alternative form of the same gene (for example, one having an alteration in polypeptide coding potential or a regulatory mutation) can provide valuable insights into the role of the polypeptides of the present invention, or that of inappropriate expression thereof in disease. Such inappropriate expression may be of a temporal, spatial or simply quantitative nature.

The polypeptides of the present invention are expressed in tissues of the heart, skeletal muscle, liver, kidney and brain.

A further aspect of the present invention relates to antibodies. The polypeptides of the invention or their fragments, or cells expressing them, can be used as immunogens to produce antibodies that are immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256: 495–497), the trioma technique, the human B-cell hybridoma technique (Kozbor et al., Immunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above described antibodies may be employed to isolate or to identify clones expressing the polypeptide or to purify the polypeptides by affinity chromatography. Antibodies against polypeptides of the present invention may also be employed to treat diseases of the invention, amongst others.

Polypeptides and polynucleotides of the present invention may also be used as vaccines. Accordingly, in a further aspect, the present invention relates to a method for inducing an immunological response in a mammal that comprises inoculating the mammal with a polypeptide of the present invention, adequate to produce antibody and/or T cell immune response, including, for example, cytokine-producing T cells or cytotoxic T cells, to protect said animal from disease, whether that disease is already established within the individual or not. An immunological response in a mammal may also be induced by a method comprises delivering a polypeptide of the present invention via a vector directing expression of the polynucleotide and coding for the polypeptide in vivo in order to induce such an immunological response to produce antibody to protect said animal from diseases of the invention. One way of administering the vector is by accelerating it into the desired cells as a coating on particles or otherwise. Such nucleic acid vector may comprise DNA, RNA, a modified nucleic acid, or a DNA/RNA hybrid. For use a vaccine, a polypeptide or a nucleic acid vector will be normally provided as a vaccine formulation (composition). The formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions that may contain anti-oxidants, buffers, bacteriostats and solutes that render the formulation instonic with the blood of the recipient; and aqueous and non-aqueous sterile suspensions that may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention have one or more biological functions that are of relevance in one or more disease states, in particular the diseases of the invention hereinbefore mentioned. It is therefore useful to identify compounds that stimulate or inhibit the function or level of the polypeptide. Accordingly, in a further aspect, the present invention provides for a method of screening compounds to identify those that stimulate or inhibit the function or level of the polypeptide. Such methods identify agonists or antagonists that may be employed for therapeutic and prophylactic purposes for such diseases of the invention as hereinbefore mentioned. Compounds may be identified from a variety of sources, for example, cells, cell-free preparations, chemical libraries, collections of chemical compounds, and natural product mixtures. Such agonists or antagonists so-identified may be natural or modified substrates, ligands, receptors, enzymes, etc., as the case may be, of the polypeptide; a structural or functional mimetic thereof (see Coligan et al., Current Protocols in Immunology 1(2): Chapter 5 (1991)) or a small molecule. Such small molecules preferably have a molecular weight below 2,000 daltons, more preferably between 300 and 1,000 daltons, and most preferably between 400 and 700 daltons. It is preferred that these small molecules are organic molecules.

The screening method may simply measure the binding of a candidate compound to the polypeptide, or to cells or membranes bearing the polypeptide, or a fusion protein thereof, by means of a label directly or indirectly associated with the candidate compound. Alternatively, the screening method may involve measuring or detecting (qualitatively or quantitatively) the competitive binding of a candidate compound to the polypeptide against a labeled competitor (e.g. agonist or antagonist). Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Further, the screening methods may simply comprise the steps of mixing a candidate compound with a solution containing a polypeptide of the present invention, to form a mixture, measuring a PHPIP-120 activity in the mixture, and comparing the PHPIP-120 activity of the mixture to a control mixture which contains no candidate compound.

Polypeptides of the present invention may be employed in conventional low capacity screening methods and also in high-throughput screening (HTS) formats. Such HTS formats include not only the well-established use of 96- and, more recently, 384-well micotiter plates but also emerging methods such as the nanowell method described by Schullek et al, Anal Biochem., 246, 20–29, (1997).

Fusion proteins, such as those made from Fc portion and PHPIP-120 polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

Screening Techniques

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents that may inhibit or enhance the production of polypeptide (also called antagonist or agonist, respectively) from suitably manipulated cells or tissues.

A polypeptide of the present invention may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide that compete with the binding of the polypeptide to its receptors, if any. Standard methods for conducting such assays are well understood in the art.

Examples of antagonists of polypeptides of the present invention include antibodies or, in some cases, oligonucleotides or proteins that are closely related to the ligands, substrates, receptors, enzymes, etc., as the case may be, of the polypeptide, e.g., a fragment of the ligands, substrates, receptors, enzymes, etc.; or a small molecule that bind to the polypeptide of the present invention but do not elicit a response, so that the activity of the polypeptide is prevented.

Screening methods may also involve the use of transgenic technology and PHPIP-120 gene. The art of constructing transgenic animals is well established. For example, the PHPIP-120 gene may be introduced through microinjection into the male pronucleus of fertilized oocytes, retroviral transfer into pre- or post-implantation embryos, or injection of genetically modified, such as by electroporation, embryonic stem cells into host blastocysts. Particularly useful transgenic animals are so-called "knock-in" animals in which an animal gene is replaced by the human equivalent within the genome of that animal. Knock-in transgenic animals are useful in the drug discovery process, for target validation, where the compound is specific for the human target. Other useful transgenic animals are so-called "knock-out" animals in which the expression of the animal ortholog of a polypeptide of the present invention and encoded by an endogenous DNA sequence in a cell is partially or completely annulled. The gene knock-out may be targeted to specific cells or tissues, may occur only in certain cells or tissues as a consequence of the limitations of the technology, or may occur in all, or substantially all, cells in the animal. Transgenic animal technology also offers a whole animal expression-cloning system in which introduced genes are expressed to give large amounts of polypeptides of the present invention.

Screening kits for use in the above described methods form a further aspect of the present invention. Such screening kits comprise:

(a) a polypeptide of the present invention;
(b) a recombinant cell expressing a polypeptide of the present invention;
(c) a cell membrane expressing a polypeptide of the present invention; or
(d) an antibody to a polypeptide of the present invention;

which polypeptide is preferably that of SEQ ID NO:2.

It will be appreciated that in any such kit, (a), (b), (c) or (d) may comprise a substantial component.

Glossary

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide" generally refers to any polyribonucleotide (RNA) or polydeoxribonucleotide (DNA), which may be unmodified or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any polypeptide comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques that are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, 1–12, in Post-translational Covalent Modification of Proteins, B. C. Johnson, Ed., Academic Press, New York, 1983; Seifter et al., "Analysis for protein modifications and nonprotein cofactors", Meth Enzymol, 182, 626–646, 1990, and Rattan et al., "Protein Synthesis: Post-translational Modifications and Aging", Ann NY Acad Sci, 663, 48–62, 1992).

"Fragment" of a polypeptide sequence refers to a polypeptide sequence that is shorter than the reference sequence but that retains essentially the same biological function or activity as the reference polypeptide. "Fragment" of a polynucleotide sequence refers to a polynucleotide sequence that is shorter than the reference sequence of SEQ ID NO:1.

"Variant" refers to a polynucleotide or polypeptide that differs from a reference polynucleotide or polypeptide, but retains the essential properties thereof. A typical variant of a polynucleotide differs in nucleotide sequence from the reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from the reference polypeptide. Generally, alterations are limited so that the sequences of the reference polypeptide and the variant are closely similar overall and, in many regions, identical. A variant and reference polypeptide may differ in amino acid sequence by one or more substitutions, insertions, deletions in any combination. A substituted or inserted amino acid residue may or may not be one encoded by the genetic code. Typical conservative substitutions include Gly, Ala; Val, Ile, Leu; Asp, Glu; Asn, Gin; Ser, Thr; Lys, Arg; and Phe and Tyr. A variant of a polynucleotide or polypeptide may be naturally occurring such as an allele, or it may be a variant that is not known to occur naturally. Non-naturally occurring variants of polynucleotides and polypeptides may be made by mutagenesis techniques or by direct synthesis. Also included as variants are polypeptides having one or more post-translational modifications, for instance glycosylation, phosphorylation, methylation, ADP ribosylation and the like. Embodiments include methylation of the N-terminal amino acid, phosphorylations of serines and threonines and modification of C-terminal glycines.

"Allele" refers to one of two or more alternative forms of a gene occurring at a given locus in the genome.

"Polymorphism" refers to a variation in nucleotide sequence (and encoded polypeptide sequence, if relevant) at a given position in the genome within a population.

"Single Nucleotide Polymorphism" (SNP) refers to the occurrence of nucleotide variability at a single nucleotide position in the genome, within a population. An SNP may occur within a gene or within intergenic regions of the genome. SNPs can be assayed using Allele Specific Amplification (ASA). For the process at least 3 primers are required. A common primer is used in reverse complement to the polymorphism being assayed. This common primer can be between 50 and 1500 bps from the polymorphic base. The other two (or more) primers are identical to each other except that the final 3' base wobbles to match one of the two (or more) alleles that make up the polymorphism. Two (or more) PCR reactions are then conducted on sample DNA, each using the common primer and one of the Allele Specific Primers.

"Splice Variant" as used herein refers to cDNA molecules produced from RNA molecules initially transcribed from the same genomic DNA sequence but which have undergone alternative RNA splicing. Alternative RNA splicing occurs when a primary RNA transcript undergoes splicing, generally for the removal of introns, which results in the production of more than one mRNA molecule each of that may encode different amino acid sequences. The term splice variant also refers to the proteins encoded by the above cDNA molecules.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotide or two polypeptide sequences, respectively, over the length of the sequences being compared.

"% Identity"—For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

"Similarity" is a further, more sophisticated measure of the relationship between two polypeptide sequences. In general, "similarity" means a comparison between the amino acids of two polypeptide chains, on a residue by residue basis, taking into account not only exact correspondences between a between pairs of residues, one from each of the sequences being compared (as for identity) but also, where there is not an exact correspondence, whether, on an evolutionary basis, one residue is a likely substitute for the other. This likelihood has an associated "score" from which the "% similarity" of the two sequences can then be determined.

Methods for comparing the identity and similarity of two or more sequences are well known in the art. Thus for instance, programs available in the Wisconsin Sequence Analysis Package, version 9.1 (Devereux J et al, Nucleic Acids Res, 12, 387–395, 1984, available from Genetics Computer Group, Madison, Wis., USA), for example the programs BESTFIT and GAP, may be used to determine the % identity between two polynucleotides and the % identity and the % similarity between two polypeptide sequences. BESTFIT uses the "local homology" algorithm of Smith and Waterman (J Mol Biol, 147, 195–197, 1981, Advances in Applied Mathematics, 2, 482–489, 1981) and finds the best single region of similarity between two sequences. BEST-FIT is more suited to comparing two polynucleotide or two polypeptide sequences that are dissimilar in length, the program assuming that the shorter sequence represents a portion of the longer. In comparison, GAP aligns two sequences, finding a "maximum similarity", according to the algorithm of Neddleman and Wunsch (J Mol Biol, 48, 443–453, 1970). GAP is more suited to comparing sequences that are approximately the same length and an alignment is expected over the entire length. Preferably, the parameters "Gap Weight" and "Length Weight" used in each program are 50 and 3, for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S F et al, J Mol Biol, 215, 403–410, 1990, Altschul S F et al, Nucleic Acids Res., 25:389–3402, 1997, available from the National Center for Biotechnology Information (NCBI), Bethesda, Md., USA and accessible through the home page of the NCBI at www.ncbi.nim.nih.gov) and FASTA (Pearson W R, Methods in Enzymology, 183, 63–99, 1990; Pearson W R and Lipman D J, Proc Nat Acad Sci USA, 85, 2444–2448,1988, available as part of the Wisconsin Sequence Analysis Package).

Preferably, the BLOSUM62 amino acid substitution matrix (Henikoff S and Henikoff J G, Proc. Nat. Acad. Sci. USA, 89, 10915–10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a reference polynucleotide or a polypeptide sequence, the query and the reference sequence being optimally aligned and the parameters of the program set at the default value, as hereinbefore described.

"Identity Index" is a measure of sequence relatedness which may be used to compare a candidate sequence (polynucleotide or polypeptide) and a reference sequence. Thus, for instance, a candidate polynucleotide sequence having, for example, an Identity Index of 0.95 compared to a reference polynucleotide sequence is identical to the reference sequence except that the candidate polynucleotide sequence may include on average up to five differences per each 100 nucleotides of the reference sequence. Such differences are selected from the group consisting of at least one nucleotide deletion, substitution, including transition and transversion, or insertion. These differences may occur at the 5' or 3' terminal positions of the reference polynucleotide sequence or anywhere between these terminal positions, interspersed either individually among the nucleotides in the reference sequence or in one or more contiguous groups within the reference sequence. In other words, to obtain a polynucleotide sequence having an Identity Index of 0.95 compared to a reference polynucleotide sequence, an average of up to 5 in every 100 of the nucleotides of the in the reference sequence may be deleted, substituted or inserted, or any combination thereof, as hereinbefore described. The same applies mutatis mutandis for other values of the Identity Index, for instance 0.96, 0.97, 0.98 and 0.99.

Similarly, for a polypeptide, a candidate polypeptide sequence having, for example, an Identity Index of 0.95 compared to a reference polypeptide sequence is identical to the reference sequence except that the polypeptide sequence may include an average of up to five differences per each 100 amino acids of the reference sequence. Such differences are selected from the group consisting of at least one amino acid deletion, substitution, including conservative and non-conservative substitution, or insertion. These differences may occur at the amino- or carboxy-terminal positions of the reference polypeptide sequence or anywhere between these terminal positions, interspersed either individually among the amino acids in the reference sequence or in one or more contiguous groups within the reference sequence. In other words, to obtain a polypeptide sequence having an Identity Index of 0.95 compared to a reference polypeptide sequence, an average of up to 5 in every 100 of the amino acids in the reference sequence may be deleted, substituted or inserted, or any combination thereof, as hereinbefore described. The same applies mutatis mutandis for other values of the Identity Index, for instance 0.96, 0.97, 0.98 and 0.99.

The relationship between the number of nucleotide or amino acid differences and the Identity Index may be expressed in the following equation:

$$n_a \leq x_a - (x_a \cdot I),$$

in which:
$n_a$ is the number of nucleotide or amino acid differences,
$x_a$ is the total number of nucleotides or amino acids in SEQ ID NO:1 or SEQ ID NO:2, respectively,
I is the Identity Index,
· is the symbol for the multiplication operator, and
in which any non-integer product of $x_a$ and I is rounded down to the nearest integer prior to subtracting it from $x_a$.

"Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Ortholog" refers to a polynucleotide or polypeptide that is the functional equivalent of the polynucleotide or polypeptide in another species. "Paralog" refers to a polynucleotideor polypeptide that within the same species which is functionally similar.

"Fusion protein" refers to a protein encoded by two, unrelated, fused genes or fragments thereof. Examples have been disclosed in U.S. Pat. Nos. 5,541,087, 5,726,044. In the case of Fc-PHPIP-120, employing an immunoglobulin Fc region as a part of a fusion protein is advantageous for performing the functional expression of Fc-PHPIP-120 or fragments of PHPIP-120, to improve pharmacokinetic properties of such a fusion protein when used for therapy and to generate a dimeric PHPIP-120. The Fc-PHPIP-120 DNA construct comprises in 5' to 3' direction, a secretion cassette, i.e. a signal sequence that triggers export from a mammalian cell, DNA encoding an immunoglobulin Fc region fragment, as a fusion partner, and a DNA encoding PHPIP-120 or fragments thereof. In some uses it would be desirable to be able to alter the intrinsic functional properties (complement binding, Fc-Receptor binding) by mutating the functional Fc sides while leaving the rest of the fusion protein untouched or delete the Fc part completely after expression.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Further Examples

Plasmid Constructs (All Plasmids were Verified by Sequencing)

Cloning of pDBLeu—PHP1

The cDNA encoding PHP1 was amplified by PCR using the primers Hispase-Sal-up (SEQ ID NO: 3, primer 1) and Hispase-Not-low (SEQ ID NO: 4, primer 2) and ligated into vector pCR2.1TOPO (Invitrogen). Subsequently, the vector was cleaved using Sal1 and Not1 and the PHP1-encoding fragment was ligated into pDBLeu.

Cloning of pLexA-MCS—PHP1

Oligonucleotide primer 3 Y2H-MCS1 (SEQ ID NO: 5) and primer 4 SEQ ID NO. 6 Y2H-MCS2 were annealed and ligated into EcoR1 and Sal1 restingated vector pLexA (Clontech) to generate Vector pLexA-MCS containing unique EcoR1, Sal1, Xho1 and Not1 restriction sites.

A fragment encoding PHP1 was isolated from Vector pDBLeu-PHP1 using Not1 and Sal1 and ligated into Vector pLexA-MCS to generate pLexA-MCS-PHP1. All vectors were confirmed by sequencing.

Fusionproteins

The peptide sequence of the Gal4-PHP1 fusion protein is given in SEQ ID NO: 7 comprising the Gal4 protein and a C-terminally linked full length PHP-1 protein. The corresponding peptide sequence of the LexA-PHP-1 fusion protein comprised the LexA protein sequence and a C-terminally linked full length PHP-1 protein. The sequence has been disclosed in SEQ ID NO: 8.

Yeast-Two Hybrid Screen to Select PHP1-Interacting Proteins.

The yeast two-hybrid screening method is technically simple and very rapid such that several million of library clones can be screened in just a few days. All of the elements of the system are commercially available. In the screen, the His3 indicator gene will only be activated if the DNA binding domain of Gal4 (AA 1–147) and the Gal4 transactivation domain (AA 768–881) fused to the NLS of the SV40 large T antigen are brought into contact by the receptor Histidine Phosphatase and a protein ligand interaction. Although the ligands isolated from this screen bind to Histidine Phosphatase the binding partners have been confirmed in a second different—LexA-based Yeast-Two Hybrid selection scheme. If both screening procedures are implemented concurrently, ligands obtained may be tested in other systems.

A yeast Two Hybrid screen (Proquest, Life Technologies) using pDBLeu-PHP1 as bait construct and a HELA-based cDNA library as prey was performed as described (selection was performed on -Trp, -Leu, -His Minimalmedium containing 25 mM 3-Aminotriazole). Interaction was confirmed on Medium lacking Uracile, Tryptophane and Leucine as described in the manufacturers protocoll.

One positive clone representing a PHPIP-120—gene product was isolated and sequenced.

Confirmation of the PHPIP-120 ligand interaction using a LexA-based Yeast-Two Hybrid selection scheme:

To confirm the interaction in a different selection scheme, the Matchmaker LexA Two-Hybrid system (Clontech) was used due to manufacturers conditions. Vector pLexA-MCS—PHP1 was used as bait. Vector pPC86-PHPIP120, which was isolated in the Gal4 based Yeast Two Hybrid system as described above was used as prey.

Interaction of p53 and large T antigen were used as positve controls in *S. cerevisiae* strain EGY48-pSH18–32.

In Silico Analysis

The gene for the PHP1 ligand identified in above mentioned yeast-two-hybrid screen is located on human chromosome 15q22-q23. The identified gene encodes a protein of 1047 AA length, with no significant sequence homology to other known proteins. While partial sequences of this gene and their corresponding virtual ORF predictions have already been deposited in the databank a protein function as revealed in this study has not been described previously.

The invention claimed is:

1. An isolated protein histidine phosphatase interacting partner of 120 kd (PHPIP-120) polypeptide selected from the group consisting of:
   (a) a polypeptide encoded by a polynucleotide comprising the sequence of SEQ ID NO:1;
   (b) a polypeptide comprising a polypeptide sequence having at least 95% identity along its entire length to the polypeptide sequence of SEQ ID NO:2;
   (c) a polypeptide having at least 95% identity along its entire length to the polypeptide sequence of SEQ ID NO:2; and
   (d) the polypeptide sequence of SEQ ID NO:2,
   wherein each of the said PHPIP-120 polypeptides of (a) to (d) has the ability to bind specifically to the protein histidine phosphatase 1 (PHP1) having the amino acid sequence shown in SEQ ID NO:8.

2. The polypeptide of claim 1 comprising the polypeptide sequence of SEQ ID NO:2.

3. The polypeptide of claim 1 which is the polypeptide sequence of SEQ ID NO:2.

4. An isolated polynucleotide selected from the group consisting of:

(a) a polynucleotide comprising a polynucleotide sequence having at least 95% identity along its entire length to the polynucleotide sequence of SEQ ID NO:1 and which encodes a polypeptide;
   (b) a polynucleotide having at least 95% identity along its entire length to the polynucleotide of SEQ ID NO:1 and which encodes a polypeptide;
   (c) a polynucleotide comprising a polynucleotide sequence encoding a polypeptide sequence having at least 95% identity along its entire length to the polypeptide sequence of SEQ ID NO:2;
   (d) a polynucleotide having a polynucleotide sequence encoding a polypeptide sequence having at least 95% identity along its entire length to the polypeptide sequence of SEQ ID NO:2;
   (e) a polynucleotide which is the RNA equivalent of a polynucleotide of (a) to (d); and
   (f) a polynucleotide sequence complementary over its entire length to said polynucleotide of any one of (a) to (d) wherein each of the said encoded polypeptide has the ability to bind specifically to the PHP1 having the amino acid sequence shown in SEQ ID NO:8.

5. A polynucleotide of claim 4 selected from the group consisting of:
  (a) a polynucleotide comprising the polynucleotide of SEQ ID NO:1;
  (b) the polynucleotide of SEQ ID NO:1;
  (c) a polynucleotide comprising a polynucleotide sequence encoding the polypeptide of SEQ ID NO:2; and
  (d) a polynucleotide encoding the polypeptide of SEQ ID NO:2.

6. An expression vector comprising a polynucleotide which encodes a polypeptide of claim 1 when said expression vector is present in a compatible host cell.

7. A recombinant host cell comprising the expression vector of claim 6.

8. A process for producing a PHPIP-120 polypeptide, comprising culturing a host cell as defined in claim 7 under conditions sufficient for the production of said polypeptide and recovering said polypeptide from the culture.

9. A fusion protein comprising an immunoglobulin Fc-region covalently linked to a polypeptide of claim 1.

10. A method for screening or identifying compounds that stimulate or inhibit the function or level of the polypeptide of claim 1 comprising a method selected from the group consisting of:
  (a) measuring the binding of a candidate compound to the polypeptide or a fusion protein thereof by means of a label, wherein said label is directly or indirectly associated with the candidate compound;
  (b) measuring the competition of binding of a candidate compound to the polypeptide or a fusion protein thereof in the presence of a labeled competitor;
  (c) testing whether the candidate compound results in a signal generated by activation or inhibition of the polypeptide, using detection systems appropriate to the cells or cell membranes expressing the polypeptide;
  (d) mixing a candidate compound with a solution containing a polypeptide of claim 1, to form a mixture, measuring activity of the polypeptide in the mixture, and comparing the activity of the mixture to a control mixture which contains no candidate compound; and
  (e) detecting the effect of a candidate compound on the production of mRNA encoding said polypeptide or said polypeptide in cells.

11. A polypeptide of claim 1(b) or 1(c), wherein said polypeptide is encoded by a polynucleotide sequence which hybridizes along its entire length to the complement of SEQ ID NO:1 under hybridization conditions comprising overnight incubation at 42° in a solution comprising: 50% formamide, 5×SSC (150 mM NaCl, 15 mM trisodium citrate), 50 mM sodium phosphate (pH 7.5), 5×Denhardt's solution, 10% dextran sulfate, and 20 microgram/ml denatured, sheared salmon sperm DNA; followed by washing the filters in 0.1×SSC at 65° C.

12. A polynucleotide of claim 4(a), 4(b), 4(c), or 4(d), wherein said polynucleotide hybridizes along its entire length to the complement of SEQ ID NO:1 under hybridization conditions comprising overnight incubation at 42° in a solution comprising: 50% formamide, 5×SSC (150 mM NaCl, 15 mM trisodium citrate), 50 mM sodium phosphate (pH 7.5), 5×Denhardt's solution, 10% dextran sulfate, and 20 microgram/ml denatured, sheared salmon sperm DNA; followed by washing the filters in 0.1×SSC at 65° C.

13. A method of detecting the presence of a PHPIP-120 polypeptide, comprising:
  contacting a polypeptide of claim 1 with an antibody which is immunospecific for said PHPIP-120 polypeptide, and
  detecting the presence said polypeptide, when said antibody is binding to said polypeptide.

14. An isolated protein histidine phosphatase interacting partner of 120 kd (PHPIP-120) polypeptide selected from the group consisting of:
  (a) a polypeptide comprising a polypeptide sequence having at least 98% identity along its entire length to the polypeptide sequence of SEQ ID NO:2; and
  (b) a polypeptide having at least 98% identity along its entire length to the polypeptide sequence of SEQ ID NO:2; wherein each of the said polypeptides of (a) to (b) has the ability to bind specifically to the protein histidine phosphatase 1 (PHP1) having the amino acid sequence shown in SEQ ID NO:8.

15. An isolated protein histidine phosphatase interacting partner of 120 kd (PHPIP-120) polypeptide selected from the group consisting of:
  (a) a polypeptide comprising a polypeptide sequence having at least 99% identity along its entire length to the polypeptide sequence of SEQ ID NO:2; and
  (b) a polypeptide having at least 99% identity along its entire length to the polypeptide sequence of SEQ ID NO:2;
    wherein each of the said polypeptides of (a) to (b) has the ability to bind specifically to the protein histidine phosphatase 1 (PHP1) having the amino acid sequence shown in SEQ ID NO:8.

16. An isolated protein histidine phosphatase interacting partner of 120kd polypeptide which consists of a polypeptide sequence of SEQ ID NO:2.

\* \* \* \* \*